(12) United States Patent
Gräfe et al.

(10) Patent No.: US 8,815,931 B2
(45) Date of Patent: Aug. 26, 2014

(54) ORAL FORMULATIONS FOR TETRAPYRROLE DERIVATIVES

(75) Inventors: Susanna Gräfe, Jena (DE); Nikolay Nifantiev, Moscow (RU); Albrecht Volker, Bergholz Rehbrücke (DE); Wolfgang Neuberger, Dubai (AE); Gerhard Wieland, Jena (DE); Dietrich Scheglmann, Jena (DE); Alfred Fahr, Cölbe (DE); Arno Wiehe, Berlin (DE)

(73) Assignee: Biolitec Pharma Marketing Ltd, F.T. Labuou (MY)

( * ) Notice: Subject to any disclaimer, the term of this patent is extended or adjusted under 35 U.S.C. 154(b) by 371 days.

(21) Appl. No.: 12/768,244

(22) Filed: Apr. 27, 2010

(65) Prior Publication Data

US 2010/0273803 A1 Oct. 28, 2010

Related U.S. Application Data

(60) Provisional application No. 61/173,487, filed on Apr. 28, 2009.

(51) Int. Cl.
  *A61K 31/40* (2006.01)
  *A61K 9/127* (2006.01)
  *A61K 31/498* (2006.01)
  *A61K 9/00* (2006.01)
  *A61K 31/409* (2006.01)

(52) U.S. Cl.
  CPC .............. *A61K 31/409* (2013.01); *A61K 9/127* (2013.01); *A61K 31/498* (2013.01); *A61K 9/0065* (2013.01); *A61K 9/1271* (2013.01)
  USPC ...................................................... 514/410

(58) Field of Classification Search
  CPC ................................................. A61K 41/0076
  USPC ........................................................ 514/410
  See application file for complete search history.

(56) References Cited

U.S. PATENT DOCUMENTS

| 6,054,136 | A | * | 4/2000 | Farah et al. | 424/400 |
| 2004/0180096 | A1 | * | 9/2004 | Prasad et al. | 424/490 |
| 2008/0056996 | A1 | * | 3/2008 | Simkim et al. | 424/9.2 |

OTHER PUBLICATIONS

Keck CM, Müller RH. Drug nanocrystals of poorly soluble drugs produced by high pressure homogenisation. Eur J Pharm Biopharm. Jan. 2006;62(1):3-16.*

(Continued)

*Primary Examiner* — Paul Zarek
(74) *Attorney, Agent, or Firm* — Bolesh J. Skutnik; B J Associates (57) ABSTRACT

Oral formulations and method of formulating photosensitive agents for oral administration during photodynamic therapy (PDT) and Antimicrobial photodynamic therapy (APDT) treatment are presented. The oral formulated photosensitizers show increased solubility and permeability, thus improving the bioavailability of photosensitizers at the treatment site. An orally administered photosensitizer is suitably formulated for mucosal adhesion and absorption via gastrointestinal mucosal membranes. Oral formulation provided herein use lipids and known proteins as carriers for photosensitizers by oral route. Carriers for encapsulating preselected photosensitizers include conventional liposomes, pegylated liposomes, nanoemulsions, nanocrystrals, nanoparticles, fatty emulsions, lipidic formulations, hydrosols, SMEDDS, Alpha-Feto protein (AFP), and Bovine-Serum-Albumin (BSA), fatty emulsions, hot-melt-extrudates and nanoparticles. The oral formulation, in case of a hydrophobic photosensitizer in the present invention, is stabilized using suitable surfactants/solubilizers thus preventing aggregation of the drug in the stomach and until it is absorbed in the duodenum and the small intestine. Oral formulations can be administered in the form of liquid, capsule, tablet, powder, paste or gel. Formulated drugs can be administered orally as one single dose or in multiple doses before administering PDT. In one embodiment Temoporfin (m-THPC) is used as a photosensitizer in the oral formulations. Temoporfin like many hydrophobic photosensitizers are especially suitable to be administered orally because there is no known enzyme system in the mammalian body which can metabolize Temoporfin or similar photosensitizers. Temoporfin can reach the blood system unchanged and fully active after absorption of the formulation in the gastrointestinal tract.

5 Claims, 2 Drawing Sheets

(56) References Cited

OTHER PUBLICATIONS

Dragicevic-Curic N, Gräfe S, Albrecht V, Fahr A. Topical application of temoporfin-loaded invasomes for photodynamic therapy of subcutaneously implanted tumours in mice: a pilot study. J Photochem Photobiol B. Apr. 25, 2008;91(1):41-50. Epub Feb. 1, 2008.*

* cited by examiner

TETRAPYRROLE MACROCYCLES

Porphyrin

Chlorin (17,18-dihydroporphyrin)

Bacteriochlorin (7,8,17,18-tetrahydroporphyrin)

Porphyrinogen

Isobacteriochlorin (12,13,17,18-tetrahydroporphyrin)

Corrole

Phthalocyanine

2,3-Dihydro-2,3-dihydroxy-15,20-dihexyl-5,10-bis(4-carboxyphenyl)porphyrin
FIGURE 3

ORAL FORMULATIONS FOR TETRAPYRROLE DERIVATIVES

DOMESTIC PRIORITY Under 35 USC 119(e)

This application claims the benefit and priority of U.S. Provisional Application Ser. No. 61/173,487 filed Apr. 28, 2009, entitled "New Oral Formulations for Tetrapyrrole Derivatives" by Susanna Grate et al., which is incorporated by reference herein.

BACKGROUND OF THE INVENTION

1. Field of the Invention Present invention generally relates to drug formulation. In particular it relates to an oral formulation of tetrapyrrole compounds and their derivatives, to be used in the photodynamic therapy (PDT), Antimicrobial Photodynamic therapy (APDT) and even for photodiagnosis purpose. This formulation will be administered orally.

2. Invention Disclosure Statement

Photosensitizers are compounds which can be photoactivated by irradiation of specific wavelength matching the absorption spectrum of the photosensitizer. Photosensitizers are used in Photodynamic Therapy (PDT) treatment, a novel method used initial in treating cancer and now found to be effective in treating other medical problems also. PDT method is used to treat different kinds of cancers including proliferating and non-proliferating types, Benign Prostate Hyperplasia (BPH), other Inflammatory conditions, cosmetic applications and others. Generally photosensitizers are administered to patient systemically and topically, which both have their own merits and demerits.

In general, photosensitizers are now delivered topically or intravenously. Especially, the intravenous delivery poses problems for the medical treatment as many photosensitizers are hydrophobic or amphiphilic substances which are non-soluble in water. Sometimes the photosensitizers are administered in alcoholic solution (ethanol, propylene glycol) as e.g. the photosensitizer temoporfin. However, the alcohol content can induce pain during administration and alcohol as a solubilizing agent in general is not feasible for certain groups of patients. Therefore, there have been efforts to formulate hydrophobic photosensitizers in a way that renders them water-soluble. These approaches include many different carrier systems such as liposomes, nanoparticles, quantum dots, or carrier systems based on inorganic materials. Of special interest in this respect are carrier systems based on highly biocompatible materials such as lipids, proteins or biocompatible polymers. There are a number of such carrier systems known in the art (F. L. Primo, P. P. Macaroff, Z. G. M. Lacava, R. B. Azevedo, P. C. Marais, A. C. Tedesco, Binding and photophysical studies of biocompatible magnetic fluid in biological medium and development of magnetic nanoemulsion: A new candidate for cancer treatment. *J. Magnetism Magn. Mater.*, 2007, 310, 2838-2840; patent application WO 06133271A2; A. J. Gomes, C. N. Lunardi, A. C. Tedesco, Characterization of biodegradable poly(D,L-lactide-co-glycolide) nanoparticles loaded with bacteriochlorophyll-a for photodynamic therapy, *Photomed. Laser Surg.,* 2007, 25, 428-435; E. Ricci-Junior, J. M. Marchetti, Preparation, characterization, photocytotoxicity assay of PLGA nanoparticles containing zinc(II) phthalocyanine for photodynamic therapy use, *J. Microencapsul.,* 2006, 23, 523-538; E. Ricci-Junior, J. M. Marchetti, Zinc(II) phthalocyanine loaded PLGA nanoparticles for photodynamic therapy use, *Int. J. Pharm.,* 2006, 310, 187-195; V. Saxena, M. Sadoqi, J. Shao, Polymeric nanoparticulate delivery system for indocyanine green: Biodistribution in healthy mice, *Int. J. Pharm.,* 2006, 308, 200-204; A. Vargas, B. Pegaz, E. Debefve, Y. Konan-Kouakou, N. Lange, J.-P. Ballini, H. van den Bergh, R. Gurny, F. Delie, Improved photodynamic activity of porphyrin loaded into nanoparticles: an in vivo evaluation using chick embryos, *Int. J. Pharm.,* 2004, 286, 131-145; Y. N. Konan, M. Berton, R. Gurny, E. Allémann, Enhanced photodynamic activity of meso-tetra(4-hydroxyphenyl)porphyrin by incorporation into sub-200 nm nanoparticles, *Eur. J. Pharm. Sci.,* 2003, 18, 241-249; Y. N. Konan, R. Cerny, J. Favet, M. Berton, R. Gurny, E. Allémann, Preparation and characterization of sterile sub-200 nm meso-tetra(4-hydroxyphenyl)porphyrin loaded nanoparticles for photodynamic therapy, *Eur. J. Pharm. Biopharm.,* 2003, 55, 115-124; A. Vargas, M. Eid, M. Fanchaouy, R. Gurny, F. Delie, In vivo photodynamic activity of photosensitizer-loaded nanoparticles: Formulation properties, administration parameters and biological issues involved in PDT outcome, *Eur. J. Pharm. Biopharm.,* 2008, 69, 43-53; B. Pegaz, E. Debefve, F. Borle, J.-P. Ballini, H. Van den Bergh, Y. N. Kouakou-Konan, Encapsulation of porphyrins and chlorins in biodegradable nanoparticles: The effect of dye lipophilicity on the extravasation and the photothrombic activity. A comparative study, *J. Photochem. Photobiol. B: Biology,* 2005, 80, 19-27; patent application WO 97010811A1 and patent application WO 03097096A1). However, these water-soluble carrier systems were developed for intravenous administration. They have not yet been evaluated for their potential for oral administration.

Oral administration is one of the easiest routes for drug administration and is particularity useful for patient compliance. The main hurdles faced in oral administration of drugs include biological barriers which makes it difficult for poorly water soluble drug molecules to be administered orally. Commonly the drug size, its bioavailability, the solubility and stability makes it difficult to pass through the biological barriers like the intestinal mucosa and gut epithelium. To overcome these biological barriers drug development and manufacturing units have found novel methods of formulation using more efficient delivery systems. Newer drug delivery systems are formulated to avoid the drug being accumulated in non-targeted site such as spleen and liver thus increasing dramatically the drug half life in the circulatory system. This is difficult in some cases, as well as undesirable if it is the liver for example which contains cancerous tissue.

Oral drug delivery system development has been fostered by the need to deliver medications to patients more efficiently and with fewer side effects. The oral route is found to be the most convenient route of drug administration. The oral and other therapeutic systems in human use have been validated as concepts for controlled continuous drug release which can minimize the daily dose or the number of doses of a drug required to maintain the required therapeutic effect, while minimizing unwanted pharmacological effects. Oral drug delivery systems in particular have required innovation in material science to provide biocompatible materials during prolonged contact with body tissues, bioengineering methods to develop drug delivery modules, and clinical pharmacology studies for elucidation of drug pharmacokinetics under conditions of continuous controlled drug administration.

Oral drug delivery systems/methods provide the possibility to maintain therapeutically optimum drug concentrations in plasma and target organs; and therefor eliminate the need for frequent single dose administration. Many pharmaceutical active agents used as medicines and supplements need to be stabilized and protected against degradation or oxidation activity using suitable carrier systems. The effectiveness of such agents may be improved by increasing their solubility in body fluids or by masking their unwanted properties (such as toxicity, odor, taste and other characteristics) before reaching the target organ using drug delivery systems.

Oral administration of unstable, insoluble and bad tasting active agents would require a delivery system which can stabilize the drug, avoid precipitation, and prevent early degradation. It also calls for a system which can improve the solubility. A system to mask the bad taste, reduce toxicity and side effects. Drug formulation units use different means to achieve these characteristics by using carrier system like nano-capsule, microspheres, liposomes, and pegylation. These carrier systems are made of biocompatible polymers, lipids or even natural/synthetic proteins. Natural stable proteins/lipids have been used because of their less immunogenic properties, and additionally can be used for specific targeting.

Drug delivery systems have been widely used to administer drugs with high molecular weight, having low solubility and permeability and having high susceptibility to enzymatic action in the GIT. Examples of macromolecules include peptides, proteins, nucleotides, sugars, etc. In prior art we see many such examples of using drug delivery systems for oral administration.

In U.S. Pat. No. 7,432,369 by Williams et al., discloses pyridyl-substituted Porphyrin compounds and their effective amount used in treating various disorders. They also discuss the method of administrating the drug which include oral route along with other well established methods. Composition for oral administration of their invention include tablets, lozenges, aqueous or oily suspensions, granules, powders, emulsions, capsules, syrups or elixirs. The method of formulating the oral formulation is not discussed.

Prasad, et al., in their U.S. Pat. No. 7,364,754 disclose a certain ceramic based nanoparticle agents for encapsulating hydrophobic photosensitizers used in PDT methods. Such nanoparticles entrapping drug/dyes can be administered orally, parenterally or topically. The specific photosensitizer used here is 2-devinyl-2-(1-hexyloxyethyl)pyropheophorbide.

Robinson in his U.S. Pat. No. 6,376,483 discloses use of bacteriochlorins and bacteriopurpurins and their production methods. In his disclosure he describes the oral administration of this active agents using inert diluent or with assimilable edible carrier, or it may be enclosed in hard or soft shell gelatin capsules, or compressed into tablets or incorporated directly in food. This patent basically describes new routes for synthesis of bacteriochlorins and bacteriopurpurins from symmetrical and asymmetrical mesodiacrylate porphyrins and their uses in PDT treatment.

In U.S. Patent Application No. 2007/0237827 by Sung et al., disclose a oral formulation consisting of biodegradable nanoparticles encapsulating therapeutically active agents like HMG-CoA reductase inhibitors, erythropoietin etc., to be orally delivered showing effective paracellular permeability. This patent does not discuss photosensitizer, but relates to nanoparticles as carrier for hydrophilic protein having high molecular weight which cannot easily be absorbed in the gut and also to prevent the proteases activity on the enclosed proteineous drug.

Harel in his U.S. patent Application No. 2008/044481 discloses use of microparticles for oral administration of bioactive agents like drug, protein, vitamins, probiotic organism etc. The encapsulation material can be made of oil, polysaccharides, proteins, synthetic polymers or combination of these.

In publication WO 2007/122613, by Yoav D. Livney et al., the inventors describe a method of encapsulating hydrophobic compounds including nutrients, therapeutic and cosmetic compounds and their administration via food and beverages. Especially used milk protein casein for the encapsulation.

Generally photosensitizers in the prior art are administrated systemically or topically, depending on the place of treatment and drug properties. The solubility, molecular size and stability are certain factors used to decide the mode of administration. The present invention provides a oral formulation which can be easily administered to the patient through the oral route without any complication such as pain due to needle pricks, or staining of skin due to local application etc. Present invention aims to provide a formulation which can be easily absorbed by the gastrointestinal tract.

OBJECTIVES AND BRIEF SUMMARY OF THE INVENTION

It is an objective of the present invention to provide a suitable formulation of photosensitizer for oral administration, which can deliver the therapeutic drug dosage required for photodynamic therapy and antimicrobial photodynamic therapy treatment to the target organ or body region.

It is also an objective of the present invention to provide a suitable oral formulation using a carrier system encapsulating photosensitizer which is stable in the gastrointestinal tract.

It is yet another objective, to provide a suitable oral formulation which increases the bioavailability of the drug to ensure sufficient accumulation at the target site.

It is the still another objective, of the present invention to provide oral formulation of photosensitizer which can be administered in the form of a tablet; a capsule; a liquid fill; a powder; a paste; a syrup etc.

It is also another objective of the present invention to provide oral formulation using carrier system comprising of lipids, conventional liposomes, pegylated liposomes, thermodynamically stable nano-emulsions, Alpha-feto Protein (AFP), BSA (Bovine Serum Albumin), Hydrosoles, Self-Micro-Emulsifying-Drug-Delivery-Systems (SMEDDS), fat emulsion system, nanoparticles and other known suitable carriers.

It is further objective of the present invention to provide oral formulation, which can be easily adhered on the gastrointestinal tract mucosa, where the drug subsequently will be absorbed.

Briefly stated, present invention discloses a method of formulating photosensitive agents for oral administration during photodynamic therapy (PDT) and Antimicrobial photodynamic therapy (APDT) treatment. The oral formulated photosensitizers show increased solubility and permeability, thus improving the bioavailability of photosensitizers at the treatment site. An orally administrated photosensitizer is suitable formulated for mucosal adhesion and absorption via gastrointestinal mucosal membranes. Present invention of oral formulation uses lipids and known proteins as carriers for photosensitizer by oral route. Carriers known for encapsulating photosensitizer include conventional liposome, pegylated liposome, nanoemulsion, nanocrystrals, nanoparticles, fatty emulsions, lipidic formulation, hydrosols, SMEDDS, Alpha-Feto protein (AFP), and Bovine-Serum-Albumin (BSA), fatty emulsions and nanoparticles. The oral formulation in case of a hydrophobic photosensitizer in the present invention is stabilized using suitable surfactant/solubilizers thus preventing aggregation of the drug in the stomach and until it is absorbed in the duodenum and the small intestine. This formulation can be administered in the form of liquid, capsules, tablets, powder, paste or gel. Thus formulated drug can be administered orally as one single dose or in multiple doses before administering PDT. It is one of the embodiments of this invention to use Temoporfin (m-THPC) as a photosensitizer in the oral formulations. This compound is especially suitable to be administered orally because there is no known enzyme system in the mammalian body which can metabolize Temoporfin. So, Temoporfin can reach the blood system unchanged and fully active after absorption of the formulation in the gastrointestinal tract.

The above, and other objects, features and advantages of the present invention will become apparent from the following description to be read in conjunction with the accompanying drawings.

DETAILED DESCRIPTION OF PREFERRED EMBODIMENTS

Administration by the oral route is the most common and preferred method by which drugs are presented for systemic effects. In general orally taken drugs usually involve incorporating the drug into a tablet or a capsule. The tablet contains a variety of other substances apart from the drug itself, the drug needs to be compatible with these other substances. That means the chemical and physical property of the active agent needs to be well understood to choose the right inert ingredients and excipients for formulation. Other oral dosage forms comprise liquids (solutions, suspensions, and emulsions), semi-solids (pastes), and solids (tablets, capsules (soft and Hard), powders, granules, premixes and others.

Preformulation steps involve the characterization of a drug's physical, chemical, and mechanical properties in order to choose which other ingredients should be used in the preparation. Factors such as particle size, polymorphism, pH, and solubility of the active agent are taken into consideration, as all of these can influence bioavailability and hence the activity of a drug. The drug must be combined with inert additives by a method which ensures that the quantity of drug present is consistent in each dosage unit e.g. each tablet/capsules. The dosage should have a uniform appearance, with an acceptable taste, tablet hardness, or capsule disintegration.

Orally administered photosensitizer undergoes dissolution followed by absorption through a biological membrane into systemic circulation. The main processes effecting the oral bioavailability of a drug are dissolution, permeability, enzymatic metabolism in the gastrointestinal membranes and hepatic extraction.

Figure 1:
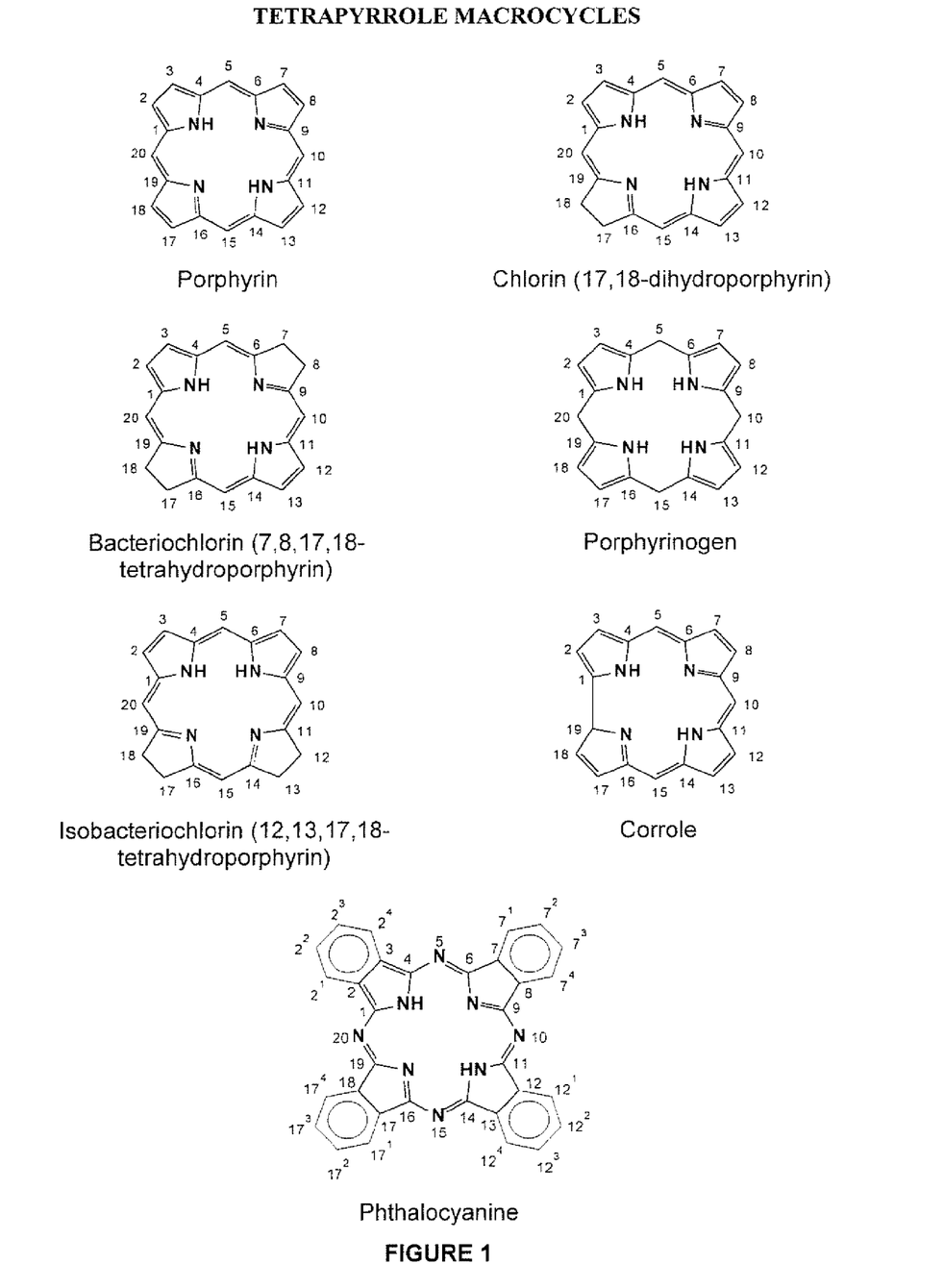
FIG. 1: examples of tetra-pyrrole skeletons in the molecules useful in photodynamic therapy.

In the present invention of oral formulation for photosensitizer the term 'photosensitizer' used herein general includes a photosensitive compound which can be photoactivated using suitable wavelength. It includes tetrapyrroles and their derivative compounds of porphyrins, chlorins (such as Chlorophyll derivatives as well as synthetic chlorins such as temoporfin, m-tetrahydroxyphenylchlorin (mTHPC)), bacteriochlorins, corroles and phthalocyanines. It also includes tautomers in all cases and their metallates and salts. The present invention involves tetrapyrrole macrocycle having the structure shown in the FIG. 1

Preferably photosensitizers having reduced porphyrins such as dihydroporphyrins in which saturated carbon atoms are located at the non-fused carbon atoms of one of the pyrrole rings. The parent compound of this series is called chlorin, which, defined in terms of the unsubstituted porphyrin ring, is 17,18-dihydroporphyrin.

Tetrahydroporphyrins in which the saturated carbon atoms are located at nonfused carbon atoms of two diagonally opposite pyrrole rings are bacteriochlorins: tetrahydroporphyrins with adjacent pyrrole rings reduced in this way are called isobacteriochlorins.

The tetrapyrrole compound of present invention is formulated into one of the following forms, but not limited, thereto, to tablet, capsule, liquid fill capsule, powder, liquid, gel or paste form. The formulation method of present invention uses required inert ingredient from among those which are chemically compatible with the preselected photosensitizer.

Dosage forms suitable for oral administration include, by way of example and without limitation, pharmaceutically acceptable emulsions, solutions, suspensions, syrups and elixirs. As mentioned, in addition to the photosensitizer, the dosage forms may contain inert diluents commonly used in the art such as water or other solvents, solubilizing agents and emulsifiers. Besides inert diluents, the oral compositions may also include adjuvants such as wetting agents, emulsifying and suspending agents, crystallization inhibitors, preservatives, pH buffering agents, sweetening, flavouring and odor masking agents.

Pharmaceutically acceptable means the inert materials, compositions, and dosage forms which are suitable for use in tissues of human beings or animals without causing excessive toxicity, allergic response, or complication, commensurate with a reasonable benefit/risk ratio.

Pharmaceutically acceptable carriers or delivery systems useful in this disclosure include conventional as well as novel systems known in the art of drug delivery systems.

In general, dosage form of present invention includes: photosensitizer; and pharmaceutical acceptable excipient/carrier, further including fillers, binders, disintegrants, lubricants, glidants, wetting agents, buffering agent, absorption accelerator and others depending on the drug dosage form.

Tablet Form

In general a tablet formulation of tetrapyrrole compounds and its derivates will have:

Required percentage of the photosensitizer (active agent), certain percentage of surfactant, fillers, disintegrants, lubricants, glidants, binders, absorption accelerator, solution retarding agents, wetting agents, absorbents; buffering agent and small percentage of compounds which ensure easy disintegration, to avoid aggregation, and dissolution of the tablet in the gut region. The use of surfactant helps to stabilize the hydrophobic photosensitizer and avoid aggregation.

The disintegration time can be modified for a rapid effect or for sustained release. Special coatings can make the tablet resistant to the stomach acids such that it only disintegrates in the duodenum as a result of a more alkaline pH or specific enzyme action, or can cause a restricted diffusion from the tablet to the gut. Tablets can also be coated with sugar to disguise the taste. Some tablets are designed with an osmotically active core, surrounded by an impermeable membrane with a pore in it. This allows the drug to percolate out from the tablet at a constant rate as the tablet moves through the digestive tract. In one of the embodiments, mTHPC is used as a preferred photosensitizer which does not form metabolites once inside the body hence are resistant to enzymatic and other biochemical activity in vivo. ((Ref: Hony Cai et al, Biomedical Chromatography 13: pg. 354-359 (1999) and Biomedical Chromatography 13: pg. 184-186 (1999). In "The Pharmacokinetic behaviour of the photosensitizer m-THPC in mice and men by Martijn Triesscheijn et al; Cancer Chemother Pharmacol 60: Pg. 113-122 (2007) pharmacokinetics of mTHPC and its pharmacokinetic behaviour is related when bound to lipoproteins in vivo. The study reports that neither lipoprotein levels nor cholesterol metabolism affects the pharmacokinetics of mTHPC in Plasma.

In the present invention the examples of tablet core include but are not limited to maize starch, pregelatinized starch, sodium starch glycollate, povidone, glycerol dibehenate, magnesium stearate, lactose monohydrate, powdered cellulose, pregelatinized maize starch, colloidal anhydrous silica, microcrystalline cellulose, hydroxypropyl cellulose, indigo carmine aluminium lake, crospovidone, silica, colloidal anhydrous/Colloidal silicon dioxide etc.

Suitable film coating materials/compositions include but are not limited to hypromellose, glycerol triacetate, talc, titanium dioxide (E171), iron oxide yellow (E172), iron oxide red (E172), ethylcellulose, polyvinyl alcohol—partly hydrolized titanium dioxide, lecithine, xanthane gum.

Capsule Form

In one of the embodiments, a capsule, a gelatinous envelope is used to enclose the photosensitizer formulation. Capsules can be designed to remain intact for some hours after ingestion in order to delay absorption. They may also contain a mixture of slow- and fast-release particles to produce rapid and sustained absorption in the same dose. The two main types of capsules are hard-shelled capsules, used for dry, powdered ingredients, and soft-shelled capsules, used for oils and for active ingredients that are dissolved or suspended in oil. Both of these classes of capsule are made both from gelatine and from plant-based gelling substances like carrageenans and modified forms of starch and cellulose.

The Capsule shell materials used in present invention include but are not limited to hypromellose, ethylcellulose, lactose monohydrate, magnesium stearate. hypromellose, hydroxypropyl methylcellulose acetate succinate, Sucrose, sugar spheres, talcum, titanium dioxide, triethyl citrate, povidone, silica, colloidal anhydrous/colloidal silicon dioxide, polysorbate 20, etc.

Further the capsule shell material can contain pharmaceutically acceptable coloring agents for example titanium dioxide, yellow iron oxide, red iron oxide, gelatin, sodium lauryl sulfate, indigo carmine, yellow iron oxide and edible white ink. Still further the capsule shell material can contain pharmaceutically acceptable printing ink which includes but is not limited to shellac, lecithin (soya), simethicone, red iron oxide, and hydroxypropyl cellulose.

Liquid Fill Capsules (Soft and Hard Capsules)

In yet another embodiment, liquid filled capsules are used; as they improve the bioavailability of hydrophobic photosensitizer by promoting absorption. Liquid filling is particularly suitable in products containing highly potent and cytotoxic compounds due to the simplified manufacturing process and in products that exhibit low solubility or poor bioavailability in other formats. The solubilizing agents include but are not limited to Poly ethylene gycol/macrogols (Trade name Lutrol® (BASF AG))

Liquid Form-Foslipos Formulation

The term 'Foslipos' of the present invention means a lipid formulation encapsulating hydrophobic photosensitizer by forming liposomal vesicles with no added saccharide and which is not freeze dried. Lipids have an ability to solubilize hydrophobic drugs, thus lipid-based drug delivery systems have been proven to improve drug absorption and dissolution rates in the gastrointestinal tract.

Liposomal vesicles used in the present invention are composed of phospholipids, preferably synthetic phospholipids are phosphatidyl cholines; such as dipalmitoylphosphatidyl choline (DPPC), dimyristoyl phosphatidyl choline (DMPC), distearoyl phosphatidyl choline (DSPC), and phosphatidyl glycerol; such as dipalmitoyl glycerol (DPPG), distearoyl phosphatidyl glycerol (DSPG) and dimyristoyl phosphatidyl glycerol (DMPG).

Foslipos focuses on the lipid bilayer as transport compartment. In this way, the photosensitizer resides within the membrane, the photosensitizing agents are effectively targeted to their place of action but the luminal part inside the liposome particle stays free for the inclusion of other substances, including drugs that may have a beneficial effect on the therapy. The liquid liposomal formulation of photosensitizer in this invention is never freeze dried unlike the conventional liposomal formulation, nevertheless it has a long, stable viable shelf life which makes the drug commercially interesting.

Pegylated Liposomal Formulation-Liquid Form

Hydrophobic photosensitizer and typically two or more synthetic phospholipids and at least one pegylated phospholipid are dissolved in an alcoholic solution. The solution is then dried under vacuum using a rotary evaporator. The mixture is then passed through a homogenizer filter system using a final pore size of 100 nanometers. During rehydration the water is supplemented with monosaccharides. The filtrate is collected, filled into vials and optionally freeze dried.

Pegylated liposomal formulation was prepared using synthetic phospholipids. The phospholipids used in this invention preferably include DPPC (dipalmitoyl phosphatidyl choline), DPPG (dipalmitoyl phosphatidyl glycerol) and DSPE (pegylated distearoyl phosphatidyl ethanolamine), all of which are produced synthetically.

In another embodiment of the present invention an oral formulation can be produced in liquid form where the a mixture of the photosensitizer and lipofundin can be administered through oral route.

Thermodynamically Stable Nano and Self Emulsifying Microemulsion Drug Delivery System (SMEDDS)

In another embodiment an oral formulation of nano and micro-emulsion is employed for oral administration of photosensitizer. An emulsion is a liquid system in which one liquid is dispersed in a second, immiscible liquid (with or without emulsifiers), usually in droplets. SMEDDS (microemulsions system) are thermodynamically stable carrier system of hydrophobic drug shaving prolonged shelf life. Present formulations of micro-emulsion formulation are prepared using non-toxic, non-irritant and pharmaceutically acceptable ingredients.

The term SMEDDS (self emulsifying microemulsion drug delivery system) is defined as isotropic mixtures of oil, surfactant, cosurfactant and drug that rapidly form oil in water microemulsion when exposed to aqueous media or gastrointestinal fluid under conditions of gentle agitation or digestive motility that would be encountered in GI tract. The term SMEDDS is used in its conventionally accepted sense as a non-opaque or substantially non-opaque colloidal dispersion comprising water and organic components including hydrophobic (lipophilic) organic components. SMEDDS are identifiable as possessing one or more of the following characteristics. They are formed spontaneously or substantially spontaneously when their components are brought into contact, that is without substantial energy supply, e.g. in the absence of heating or the use of high shear equipment or other substantial agitation. They exhibit thermodynamic stability. They are monophasic. They are substantially non-opaque, i.e. are transparent or opalescent when viewed by optical microscopic means. In their undisturbed state they are optically isotropic. SMEDDS comprise a dispersed or particulate (droplet) phase, the particles of which are of a size less than 200 nm, hence they exhibit optical transparency. The pharmaceutical and cosmetic industries are expressing an ever increasing demand for compositions free from an aqueous phase, in order to facilitate their packaging in the form of hard gelatin capsules, tablets and plasters. The compositions known at the present time for the manufacture of hard gelatin capsules, in particular the ones described in the above documents, are unable to meet the need, since the presence of water contained in these mixtures is incompatible with the technique employing hard gelatin capsules.

The invention solves these problems. It relates to an orally administrable composition, in particular for pharmaceutical or cosmetic use, comprising a lipophilic phase, at least one surfactant and at least one cosurfactant which, mixed and in the presence of physiological fluid, form a microemulsion facilitating dissolution in situ and improving the bioavailability of the active principles.

Preparation of Formulation in General:

This orally administrable composition capable of forming a microemulsion, comprising at least:
- an active principle,
- a lipophilic phase consisting of a mixture of fatty acid esters and glycerides,
- a surfactant (SA),
- a cosurfactant (CoSA),
- a solvent,
- a hydrophilic phase, is characterized: in that the lipophilic phase consists of a mixture of C 8 to C 18 polyglycolized glycerides having a hydrophilic-lipophilic balance (HLB) of less than 16, this lipophilic phase representing from 1 to 75% of the total weight of the composition; in that the surfactant (SA) is chosen from the group comprising saturated C 8-C 10 polyglycolized glycerides and oleic esters of polyglycerol, this surfactant also having an HLB of less than 16; in that the cosurfactant (CoSA) is chosen from the group comprising lauric esters of propylene glycol, oleic esters of polyglycerol and ethyl diglycol; in that the SA/CoSA ratio is between 0.3 and 8; and in that the hydrophilic phase of the final microemulsion is supplied after ingestion by the physiological fluid of the digestive milieu.

In one another embodiment of the invention microemulsions as Self-Micro-Emulsifying-Drug-Delivery-Systems (SMEDDS) formulation can include varying amounts of photosensitizer as active agent preferably Temoporfin (mTHPC), while the excipient employed includes a non-limiting list of examples such as: macrogolglycerolhydroxystearate 40, polyethoxylated castor oil, Cremophor®EL (sold by BASF). Polyethyleneglycole 300, Polyethyleneglycole 400, d-alpha-tocopheryl-polyethyleneglycol-1000-succinate: TPGS® (sold by Estman), Caprylocaproyl Macrogolglycerides (Polyoxylglycerides): Labrasol®, Propylene Glycol Monocaprylate/Propylene Glycol Caprylate Capryol® 90, Diethylene Glycol Monoethyl Ether: Transcutol, Oleoyl Macrogolglycerides (Polyoxylglycerides)/Linoleoyl Macrogolglycerides (Polyoxylglycerides): Labrafil®, Lauroyl Macrogolglycerides (Polyoxylglycerides)/Stearoyl Macrogolglycerides (Polyoxylglycerides): Gelucire®, Glyceryl Mono-Linoleate: Maisine®, Propylene Glycol Dicaprylocaprate/Medium Chain Triglycerides: Labrafac®, Propylene Glycol Monolaurate/Propylene Glycol Laurate: Lauroglycol®, Glyceryl Mono-Oleate: Peceol®, Polyglyceryl Oleate: Plurol Oleicque® (all sold by Gattefossé SAS, St. Priest, France); Mono, -Diglycerides: Capmul® MCM, Mixed Diesters of caprylic/capric acids on propylene glycol: Captex®200, Triglycerides of caprylic/capric acid: Captex®355, Polyglycerol oleate: Caprol® MPGO, Oleic esters on Decaglycerol: Caprol® PGE-860, Ethoxylated coconut glycerol esters: Acconon®CO-7, Ethoxylated caprylic/capric glycerol esters: Acconon®CC-6 (All sold by ABITEC Corporation) and other recrystallation inhibitors, bioavailability enhancers, surfactants, emulsifiers, ethanol and water, to be mixed in several different regimes. These formulations will finally be administered filled in soft gelatine capsules. In the duodenum and small intestine the SMEDDS formulation after contact with the intestinal fluid will form single layered micelles sized to about 200 nm suitable to be absorbed easily onto the mucosa for the following uptake in the body.

Nanosuspensions

An alternative to the aforementioned way to solubilize highly unsoluble drugs is the reduction of the particle size, which leads to an increased surface area and therefore the dissolution rate increases. However, micronization alone is not sufficient to attain the desired bioavailability for these kind of drugs. Nanonisation has shown to provide higher bioavailability of drugs if the particle size is in the sub-micrometer size range (Müller et al., 1998, 2001] because it increases drug dissolution rate and the saturation solubility of the compound. There are different methods described in the literature for reducing the particle size of drug particles to a nanometer range, for example precipitation ([Trotta et al., 2001], jet milling, pearl milling (Liversidge and Conzentino, 1995) and high-pressure homogenization (Müller & Keck, 2004).

To transform aqueous dispersions into dry powder, one can use lyophilization and spray drying procedures. Spray drying usually requires high temperature in the process, which is not suitable for thermolabile drugs. In such cases, lyophilization is the most suitable procedure. In the lyophilization process, a cryoprotective agent such as mannitol, trehalose or sucrose is added to the solution to avoid particle aggregation after reconstitution of the system.

O/W Emulsion Formulation

In another embodiment of the present patent the formulation principle to be administered orally is a mixture of oil and fat compounds with mTHPC. Such emulsions containing soya oil, medium-chain triglycerides, glycerol, egg lecithin, α-Tocopherol, sodium oleate and water in different concentrations are used clinically as a calory sources in i.v. nutrition.

Hot-Melt-Extrusion Formulation

In another embodiment of the present invention the formulation principle to be administered orally is a mixture of biocompatible polymers blended with suitable excipients with mTHPC. These mixtures will be molten up homogenously, extruded through a single or twin-screw extruder to form solid dispersions of the API.

These solid dispersions show higher solubility rates of the API due to higher grades of wettability and bioavailability, thus improving the drug release in the GIT. Suitable polymers could be chosen non-exclusively out of the group of "basic butylated methacrylate copolymer (aPMMA)", Copovidone (COP), Polyethylene glycol-polyvinyl alcohol copolymer (PEG-PVA), Eudragit-variants and other polymers and excipients know to experts in the field of the invention.

Nanocrystal Formulation

In another embodiment of the present invention the active drug compound could be administered perorally in a nanocrystal formulation. Extremely fine grinded drug, for example Temoporfin, would be stabilized by surfactants and finally spray-dried to retain their large surface which facilitates resorption in the gastrointestinal tract stably.

Powdered Form-Liposome Encapsulated Photosensitizer

In one of the embodiment of the present invention, photosensitizers are encapsulated into a liposome for oral administration. Liposomal vesicles can improve the solubility of hydrophobic photosensitizers to be administrated orally.

Liposomes were prepared according to the following general procedure:

The hydrophobic photosensitizer and typically two or more synthetic phospholipids are dissolved in alcoholic solution. The solution is then dried under vacuum using a rotary evaporator. The mixture is then passed through a homogenizer filter system using a final pore size of 100 nanometers. The rehydration water is supplemented with monosaccharides. The filtrate is collected, filled into vials and optionally freeze dried.

The synthetic Phospholipids such as phosphatidyl choline can be one or more synthetic cholines such as dipalmitoyl phosphatidyl choline (DPPC), dimyristoyl phosphatidyl choline (DMPC), distearoyl phosphatidyl choline (DSPC). Suggested glycerols include dipalmitoyl phosphatidyl glycerol (DPPG) and dimyristoyl phosphatidyl glycerol (DMPG). Certain phospholipids used here in required ratio can stabilize the liposomal formulation and protect it from gastrointestinal tract degradation action.

Thus formulated liposome encapsulating photosensitizer is in the form of dry powder which can formulated into a tablet or can be encapsulated into a hard capsule for oral administration.

Nanoparticles as a Drug Carrier System

The oral formulation may also involve nanoparticles on which the photosensitizer is absorbed, in which the photosensitizer is included or to which the photosensitizer is covalently attached. In a preferred formulation the nanoparticles are formed from biodegradable materials such as human serum albumin (HSA) or Poly(lactide-co-glycolide) (PLGA), as is known in the art.

Alpha Fetoprotein (AFP) as Carrier System

Alpha-fetoprotein (AFP) is used as a oncoshuttle in this formulation to target photosensitizer to the tumor cells. AFP is used as an oncoshuttle since most cancers express AFP receptors (AFPR), and hence are target specific. AFP is a large glycoprotein consisting of a polypeptide chain containing about 600 amino acids and a large heterogeneous carbohydrate moiety. AFP molecules contain 15 disulphide bonds. Whereas the disulphide bonds determine the tertiary structure, the carbohydrates confer the molecule with special binding properties.

Preparation of the formulation can be divided into three parts:

1) unloading the AFP-protein
2) binding of the drug substance to the protein
3) isolation of the protein-drug-complex and preservation As the protein is only available with bound lipophilic substances (for instance fatty acids), these substances have too be liberated from the protein to allow subsequent binding of the drug molecules.

Step 1. Unloading can be achieved with any organic solvent, which does not disturb the protein structure but will dissolute the lipophilic substances. Therefore watery solution of primary and secondary alcohols or polyalcohols can be used. After unloading, the AFP has to be purified by ultrafiltration.

Step 2. The loading procedure requires a solvent which is able to dissolute the drug substance and has to be removed after the incubation time. Removal can be performed by freeze drying or evaporation.

Step 3. The unbound drug substance has to be removed by ultrafiltration and the solution has to be stabilized.

Bovine-Serum-Albumin (BSA) as Carrier System

A natural protein such as Bovine-Serum-Albumin (BSA) is used in the present invention to encapsulate the photosensitizer for oral administration. The amino acid sequence of AFP has significant homologies to Bovine-Serum-Albumin. The peculiarity of albumin-like proteins is the presence of three structurally homologous domains formed by two alpha-helical globin-like subdomains. Therefore, BSA can also be used as an effective carrier in PDT. BSA is large globular protein with 17 disulphide bonds. The preparation procedure of BSA formulations is as follows:

Preparation of the formulation can be divided into three parts:

1) unloading the BSA-protein
2) binding of the drug substance to the protein
3) isolation of the protein-drug-complex and preservation As the protein is only available with bound lipophilic substances (for instance fatty acids and other lipids), these substances have too be liberated from the protein to allow subsequent binding of the drug molecules.

Step 1. Unloading can be achieved with any organic solvent, which does not disturb the protein structure but will dissolve the lipophilic substances. Therefore watery solution of primary and secondary alcohols or polyalcohols can be used. After unloading, the BSA has to be purified by ultrafiltration.

Step 2. The loading procedure requires a solvent which is able to dissolute the drug substance and has to be removed after the incubation time. Removal can be performed by freeze drying or evaporation.

Step 3. The unbound drug substance has to be removed by ultrafiltration and the solution has to be stabilized.

Present formulation methods do not limit to the above mentioned carrier systems and formulations, but it can be used with other carriers suitable for oral formulation like microspheres, polymers, micelles, hydrosoles, apasomes, and niosomes and novel technical devices like iPills etc.

The disclosed orally formulated photosensitizer is administered orally for treating different types of cancerous conditions such as head and neck cancer, prostate cancer, skin cancers and others, it also further includes proliferating and non-proliferating disorders, and other disease conditions such as BPH, dysplasia, Barrett's Oesophagus, Age Related Macular Degeneration, vascular diseases, inflammatory disorders and bacterial and viral infections. It can further be used for cosmetic application of PDT such as skin rejuvenation, acne treatment, scare and wrinkle removal, hair removal, fat reduction and cellulite treatment. It is also used in antimicrobial photodynamic therapy for treating microbial infections; such as viri, bacteria, fungi, protozoan parasites and prions. Further PDT applications include dental problems and others. The present formulation is not limited to above mentioned examples alone but can be extended to other human and animal disorders which can be treated using photodynamic therapy (PDT).

In general PDT treatment method using the present oral administration of photosensitizer involves single administration of photosensitizer via oral route followed by illumination. Further embodiment also involves use of multiple oral administration of photosensitizer followed by single illumination regime or multiple light illumination regime. The multiple oral dosages can be given daily or weekly or as required depending on the disease condition and location. The optimal drug dosage within the tissue can be ensured by measuring fluorescence before the irradiation. Such optimized treatment regime minimizes light sensitivity and maximizes usage of the drug while at the same time limiting necrosis and causing sequential killing of the target tissues. Such optimized multiple treatment regimes also help to induce immune action in the body initiating immune response against targeted cell for long. Depending on the disease condition the above treatment regime may be repeated as required after a short gap.

Further it can also be used for diagnostic purpose by orally administrating a low dosage. The term 'low' here means to say a effective dosage that is normal lower than the general administrated effective therapeutic dosages. The term 'Diagnostic' means a material useful for testing for the presence or absence of a active agent or disease, and/or a agent that enhances tissue imaging. The term 'effective' here means an oral dosage of a diagnostic or therapeutic agent that is useful for producing a desired effect.

In another possible embodiment, tetrapyrrole derivative formulations for oral administration of the present invention are used as non-PDT therapeutic agents or as anti-cancer chemotherapeutic agents without application of light/radiation. The action of the drug in the absence of the light energy is referred to as dark toxicity. The drug here acts as a cytotoxic agent acting directly on the cells. The oral formulated tetrapyrrole of the present invention is adminstered to the patient as a single dose or preferably as a multiple dose. Here the cytotoxic effect is directly dependent of the drug concentration in use and hence needs to be carefully supervised by a physician. This application would be useful for the inactivation of cancer cells, bacteria, fungi and parasites and infectious prions.

Determination of Dark Toxicity

Figure 3:
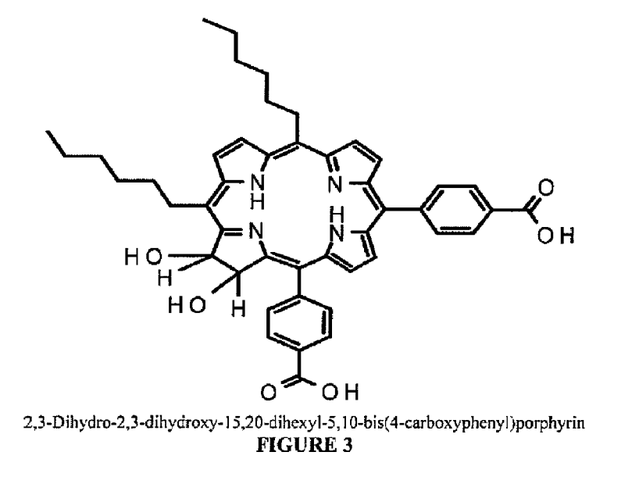
FIG. 3: Structure of BLC6066 a Photosensitive agent

Dark toxicity effect of 2,3-Dihydro-2,3-dihydroxy-15,20-dihexyl-5,10-bis(4-carboxy-phenyl)porphyrin (BLC 6066) (refer FIG. 3) in different cell lines like MG 82, HT29 and J774A1 was determined by incubating the cell culture with different increasing concentration of BLC6066 in the range of 2 to 10 μmM for about 24 hrs. Cells incubated in the concentration of 10 μM of BLC 6066 showed definite toxicity in human cells, plus strong dark toxicity towards bacteria cells.

The present invention is further illustrated by the following examples, but is not limited thereby.

EXAMPLE 1

FOSLIPOS—A Liposome Based Oral Formulation of a Hydrophobic Photosensitizer for Orally Administered Foslipos (lipid based formulation of mTHPC, containing DPPC and DPPG)

Drug Dosage: 300 μg mTHPC

Studies were performed using adult female athymic NMRI nu/nu mice (Harlan Winkelmann GmbH, Germany). Six to eight-week old mice weighing 22-24 g were inoculated subcutaneously into the left hind thigh with a suspension of HT29 human colorectal carcinoma cells (0.1 ml of $8 \times 10^7$ cells/ml in 5% glucose). Experiments were performed 10 days later, when tumors reached a surface diameter of about 5-8 mm, and a thickness of 2-3 mm in height.

Figure 2:
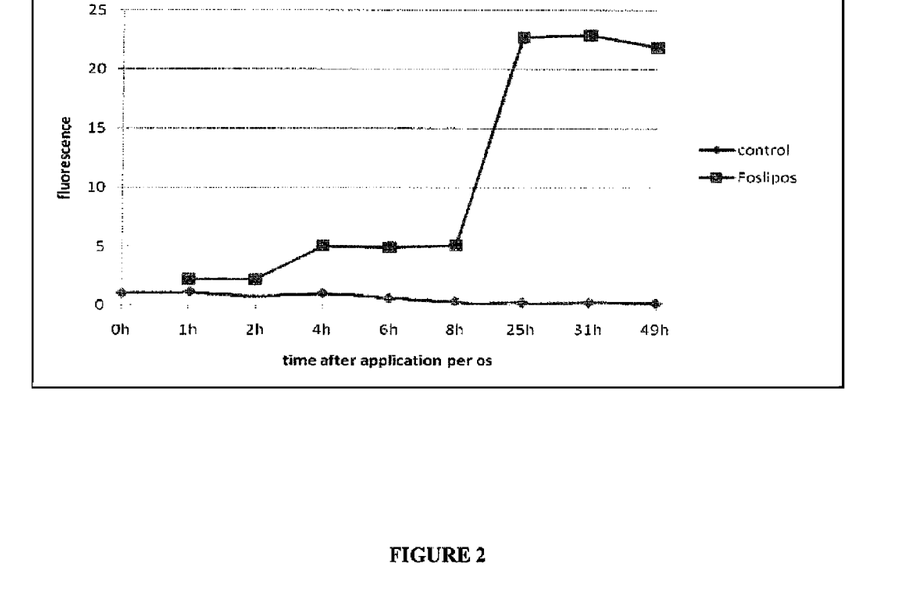
FIG. 2: A graph depicting florescence measured in a in female NMRI nu/nu mice bearing a HT29 tumor after oral application of FOSLIPOS.

Foslipos (300 μg mTHPC drug dosages) was administered by gavage. Immediately after application fluorescence of the skin was measured by a fiber spectrometer (Jeti GmbH Jena). Excitation wavelength was 415 nm, emission wavelength 652 nm. Fluorescence of the skin was measured at different time points after administration (0 h, 1 h, 2 h, 4 h, 6 h, 8 h, 25 h, 31 h and 49 h). High fluorescence values could be measured for the Foslipos from 24 h after oral application (refer FIG. 2).

HPLC Analysis

Animals were sacrificed 50 hours after oral application of Foslipos (three mice each time point). Immediately after the animals were killed the plasma, liver, spleen, colon, tumor, skin and skeletal muscle were dissected, weighed and stored at −70° C. All tissue samples were reduced to small pieces by cutting with a scalpel, weighed and freeze dried (Christ Freeze drying system Alpha 1-4 LSC). The resulting powdered tissue was weighed and approx. 10-20 mg was transferred in to a 2.0 ml reaction tube and 1.5 ml of methanol: Dimethyl sulfoxide (DMSO) (3:5, v:v) was added. The samples are mixed for five seconds using a vortex mixer (Merck Eurolab, MELB 1719) operating at 2,400 rpm and then incubated at 60° C. under continuous shaking for at least 12 hours. All samples were centrifuged at 16,000 g (Microfuge, Heraeus, Germany) for five minutes. 1 ml of each supernatant was transferred to a HPLC vial for HPLC analysis.

HPLC analysis of the sample shows higher Foslipos accumulation in tumor cells compared to other tissues readings.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. An oral formulation for a hydrophobic photosensitizer comprising a photosensitizer selected from the group consisting of temoporfin and an antibacterial photosensitizer.

2. The oral formulation according to claim 1, wherein said photosensitizer, which is resistant to stomach digestive material, does not accumulate in liver or kidneys, and further comprises an inert ingredient, where necessary; and wherein said formulation is useful for treating hyperplasic diseases and in antimicrobial therapy.

3. The oral formulation according to claim 1, further comprising excipients and where said photosensitizer is itself adsorbed on, included in or covalently attached to biodegradable nanoparticles or nanoparticles which are not metabolized in the gut.

4. The oral formulation according to claim 1, further comprising galenical excipients forming a self-micro-emulsifying-drug delivery-system (SMEDDS) with said photosensitizer.

5. The oral formulation according to claim 1, comprising a photosensitizer and suitable pharmacological acceptable surfactants, wherein the photosensitizer and the excipient are prepared in such manner by those skilled in the art to form stable nanocrystals.

* * * * *